United States Patent
Mora Vallejo et al.

(10) Patent No.: US 9,777,029 B2
(45) Date of Patent: Oct. 3, 2017

(54) PROCESS FOR OBTAINING METAL-ORGANIC MATERIALS WITH STRUCTURE TYPE MIL-101 (CR) AND MIL-101-CR-$M^{X+}$

(71) Applicant: INSTITUTO MEXICANO DEL PETRÓLEO, Mexico City (MX)

(72) Inventors: Rodolfo Juventino Mora Vallejo, México (MX); J. Ascención Montoya de la Fuente, México (MX); Georgina Cecilia Laredo Sánchez, México (MX); Edith Meneses Ruíz, México (MX); J. Jesús Castillo Munguía, México (MX); Beatriz Zapata Rendón, México (MX)

(73) Assignee: INSTITUTO MEXICANO DEL PETROLEO, Mexico City (MX)

( * ) Notice: Subject to any disclaimer, the term of this patent is extended or adjusted under 35 U.S.C. 154(b) by 0 days.

(21) Appl. No.: 14/964,478

(22) Filed: Dec. 9, 2015

(65) Prior Publication Data
US 2016/0185806 A1 Jun. 30, 2016

(30) Foreign Application Priority Data
Dec. 17, 2014 (MX) .................... MX/a/2014/015590

(51) Int. Cl.
C07F 11/00 (2006.01)
(52) U.S. Cl.
CPC .................. C07F 11/005 (2013.01)
(58) Field of Classification Search
CPC .................. C07F 11/00; C07F 7/005
USPC ............................................. 556/61
See application file for complete search history.

(56) References Cited

U.S. PATENT DOCUMENTS

| 8,168,813 B2 * | 5/2012 | Chang | B01D 53/28 428/116 |
|---|---|---|---|
| 2009/0131703 A1 | 5/2009 | Jhung et al. | |
| 2010/0273642 A1 | 10/2010 | Chang et al. | |
| 2011/0172412 A1 | 7/2011 | Serre et al. | |
| 2012/0165183 A1 | 6/2012 | Chang et al. | |

OTHER PUBLICATIONS

Hailian, Li et al., "Design and synthesis of an exceptionally stable and highly porous metal-organic framework", Letters to Nature 402 (1999) 276-279.
Ferey, G. et al., "A Chromium-Based Solid Terephthalate With Unusually Large Pore Volumes and Surface Area", Science 309, 2040 (2005).
Jiangfeng Yang et al., "Synthesis of metal organic framework MIL-101 in TMAOH-Cr(N03)3-H2BDC-H2O and Its hydrogen-storage behavior", Microporous and Mesoporous Materials 130 (2010) 174-179.
Young Kyu Hwang et al., ""Selective sutfoxidation of aryl sulfides bycoordinatively unsaturated metal centers in chromium carboxylate MIL-101"", Applied Catalysis A: General 358 (2009) 249-253.
O. I. Lebedev et al., "First Direct Imagen of Giant Pores of the Metal-Organic Framework MIL-101", Chem. Mater. 2005, 17, 652 5-652 7.

* cited by examiner

Primary Examiner — Sudhakar Katakam
Assistant Examiner — Kofi Adzamli
(74) Attorney, Agent, or Firm — Michael Best & Friedrich LLP (57) ABSTRACT

The present invention relates to a process for obtaining materials with Metal Organic atomic structure and called MOF (MOF: Metal Organic Framework) type MIL-101 (Cr) and MIL-101-Cr-$M^{X+}$ (MIL: Material from Institute Lavoisier), where $M^{X+}$ can be any metal cation, such as $Mg^{2+}$, $Al^{3+}$ or $Ti^{4+}$, using for its synthesis metal epoxides and alkoxides, avoiding the use of hydrofluoric acid (HF) or bases as synthesis controlling agents.

The process of the present invention for the preparation of materials MOF MIL-101 (Cr) and MOF MIL-101-Cr-$M^{X+}$ where $M^{X+}$ can be any metal cation, such as $Mg^{2+}$, $Al^{3+}$ or $Ti^{4+}$, consisting of:

a) Synthesizing MOF MIL-101 (Cr) with epoxides, or Synthesizing MOF MIL-101-Cr-$M^{X+}$ with metal alkoxides; and b) Purifying the synthesized MOF.

in order to obtain 100% pure materials, with a controlled mesoporosity associated with a hysteresis $P/P_0$ from 0.7 to 0.99, BET surface area from 2,500 to 3,500 $m^2/g$, pore volume from 1.1 to 2.2 $cm^3/g$, and pore diameter from 15 to 55 nm.

15 Claims, 5 Drawing Sheets

PROCESS FOR OBTAINING METAL-ORGANIC MATERIALS WITH STRUCTURE TYPE MIL-101 (CR) AND MIL-101-CR-M$^{X+}$

CROSS-REFERENCE TO RELATED APPLICATION(S)

This claims priority to Mexican Patent Application No. MX/a/2014/015590, filed on Dec. 17, 2014, the entire contents of which are fully incorporated herein by reference.

TECHNICAL FIELD

The present invention relates to a process for obtaining materials with Organic-Metal atomic structure and called MOF (Metal Organic Framework) type MIL-101-Cr and MIL-101-Cr-M$^{X+}$ (MIL: Material from Institute Lavoisier), where M$^{X+}$ can be any metal cation, such as Mg$^{2+}$, Al$^{3+}$ or Ti$^{4+}$, using for its synthesis metal epoxides and alkoxides, avoiding the use of hydrofluoric acid (HF) or bases as synthesis controlling agents.

By the synthesis process of the present invention, are obtaining materials such as MOF MIL-101-Cr and MOF MIL-101-Cr-M$^{X+}$, 100% pure, with controlled mesoporosity associated with a hysteresis P/P$_0$ from 0.7 to 0.99, BET surface area from 2,500 to 3500 m$^2$/g, pore volume from 1.1 to 2.2 cm$^3$/g, and pore diameter from 15 to 55 nm.

BACKGROUND

Materials called metal organic structures known as MOF's (Metal Organic Frameworks) are a novel class of materials because they have high porosity, various topologies and which atomic structure is formed of inorganic coordination subunits, of type MO-$^y{}_x$ (where M=Zn, Cu, Fe, Cr, etc.) which are linked by organic ligands or "linkers" that shared multiple complexing functions (e.g. carboxylates, phosphonates, etc.), which increases a unique variety of potential interactions within pores. These interactions rise from clusters of cations M$^{X+}$-O that normally have unsaturations and which can eventually generate acidic or Lewis basic sites, and on the other hand are found unsaturated or aromatic rings forming ligands and that may create interactions of kind π. Therefore these materials offer great potential both scientific and technological due to combination of features from their fragments, both organic and inorganic, whose main feature is the large specific area (up to 10,000 m$^2$/g) which can potentially develop, thus have been considered as promising materials for applications in magnetic, optical and electronic devices, catalysis, separation, gas storage, molecular recognition, and lastly in processes of selective adsorption of nitrogen molecules present in streams to the diesel production.

The first report of synthesis of a MOF, MOF-5 (Zn), was made by Hailian Li, et al. Design and synthesis of an exceptionally stable and highly porous metal-organic framework. Letters to Nature 402 (1999) 276-279, which states that said material remains crystalline and stable, which is evidenced by X-ray analysis of single crystal, when fully desolvated and calcined at a temperature of 300° C. This synthesis was achieved by sharing ideas from chemistry metal clusters and carboxylates, where a dicarboxylic ligand used in a reaction that provide super-tetrahedral clusters when are covered with monocarboxylates. Rigid and divergent character of added ligand allow joint of clusters in a three dimensional structure resulting in a structure with a large surface area and pore volume greater than that of the porous crystalline zeolites. This simple and potentially universal, synthesis strategy has been used for the preparation of new phases and composites, especially for gas storage application. MOF-5 is formed by Zn-BDC (1,4-benzenedicarboxilate), with final formula of Zn$_4$O(BDC)$_3$.(DMF)$_8$(C$_6$H$_3$Cl).

MOF called MIL-101-Cr (Cr(III) terephthalate) was originally synthesized by Férey G., et al. A Chromium-Based Solid Terephthalate With Unusually Large Pore Volumes and Surface Area. Science 309, 2040 (2005). This MOF has the particularity of developing major Langmuir surface areas (4,500-5,500 m$^2$/g), pore size (29-34 Å) and cell volume (702,000 Å$^3$). The synthesis of MOF known as MIL-101-Cr comprises reacting terephthalic acid (H$_2$BDC, 166 mg, 1 mmol) with chromium nitrate (Cr(NO$_3$)$_3$.9H$_2$O, 400 mg, 1 mmol), hydrofluoric acid (HF, 0.2 ml, 1 mmol) and water (H$_2$O, 4.8 mL, 265 mmol), under hydrothermal conditions for 8 hours at 220° C. This hydrothermal reaction produces chromium terephthalate highly crystallized green powder with formula Cr$_3$F(H$_2$O)$_2$O[(O$_2$C)—C$_6$H$_4$—(CO$_2$)$_3$]$_3$.nH$_2$O (where n≈25) based on chemical analysis. The chromium-based yield is ≈50%. The special feature of this synthesis is using hydrofluoric acid (HF) during preparation.

Subsequently, Jiangfeng Yang, et al. Synthesis of metal-organic framework MIL-101 in TMAOH-Cr(NO$_3$)$_3$-H$_2$BDC-H$_2$O and Its hydrogen-storage behavior. Microporous and Mesoporous Materials 130 (2010) 174-179, performed the synthesis of MOF MIL-101-Cr, replacing the HF by different alkali; potassium hydroxide (KOH), tetramethylammonium hydroxide (TMAOH), triethylamine ((C$_2$H$_5$)$_3$N), dimethylamine (C$_2$H$_7$N), methylamine (CH$_5$N) and ammonia (NH$_3$) to prevent recrystallization of terephthalic acid (H$_2$DBC). As a result, it was found that more stable material and with structure type MOF MIL-101-Cr was called TMAOH-Cr(NO$_3$)$_3$-H$_2$BDC-H$_2$O.

This type of MOF (MOF MIL-101-Cr) has a zeolite structure consisting of two chambers quasi-spherical cages (2.9 and 3.4 nm) accessible through windows 1.2 and 1.6 nm, as MOF Fe-MIL-101. Both materials have large surfaces and pore volumes (usually, from 3,200 to 3,900 and 1.4 to 2.1 m$^2$g$^{-1}$, respectively), also have very good resistance to common solvents and thermal stability (Fe-MIL-101 up to 180° C. and Cr-MIL-101 up to 300° C.). The atomic structure MIL-101 consists of terephthalate molecule that acts as ligand of M$_3$O-carboxylate trimers (M=Fe or Cr). These metal ions are octahedrally coordinated with water molecules in the linking terminals. It has been reported that water molecules (two water molecules per trimeric group according to elemental and thermogravimetric analysis) can be easily eliminated by thermal treatment under vacuum, thus providing coordinately unsaturated and catalytically active sites (Young Kyu Hwang, et al. Selective sulfoxidation of aryl sulfides by coordinatively unsaturated metal centers in chromium carboxylate MIL-101. Applied Catalysis A: General 358 (2009) 249-253.

In order to establish the state of the art of the MOF MIL-101, a literature review of patents was made based on the researcher who discovered and reported the material MOF MIL-101-Cr Ferey Gerard Institut Lavoisier, CNRS Unite Mixte Material for Research, University of Versailles St-Quentin, Versailles Cedex, France.

We found that the MOF material called MIL-101-Cr only appears with this name:
 Above-mentioned article by Férey G., et al. A Chromium-Based Solid Terephthalate With Unusually Large Pore Volumes and Surface Area. Science 309, 2040 (2005).

In patent application US 2009/0131703 A1, May 21, 2009, Jhung et al., claim a preparing method of porous inorganic-organic hybrid materials called Cr-BDCA-1, BDCA where is 1,4-dibenzocarboxylilic acid or also known as terephthalic acid. This preparation method is basically that reported by Férey G., et al. A Chromium-Based Solid Terephthalate With Unusually Large Pore Volumes and Surface Area. Science 309, 2040 (2005), already mentioned, which uses HF, being main difference using ultrasound for 1 min to homogenize the reaction mixture and then using a microwave oven to quickly heat reaction at 210° C. and reduce the reaction time to 3 min.

In patent application US 2010/0273642 A1, Oct. 28, 2010, Chang et al., referred to a method to functionalized porous organic-inorganic hybrid materials, especially MOF MIL-101-Cr or mesoporous organic-inorganic materials, particularly mesoporous material SBA-15. Functionalizing organic substances are related to inorganic substances, ionic liquids, and organic-inorganic hybrid substances incorporated step by step in inorganic unsaturated sites instead of hydroxyl groups for application in catalysis, adsorbents, gas storage materials, sensors, membranes, thin films and catalyst supports.

In the patent application US 2011/0172412 A1, Jul. 14, 2011, Serre et al., claim the use of the MOF MIL-101-Fe as a material prone to be reduced, to take advantage of reduced Fe to separate molecules mixtures with different unsaturation degree with a selectivity such that it can be adjusted by controlling the reduction degree of MOF MIL-101-Fe.

In the patent application US 2012/0165183 A1, Jun. 28, 2012, Chang et al., claim the synthesis of MOF MIL-101-Cr without using hydrofluoric acid, so consider it a synthesis more environmentally friendly. It also shows that the material obtained by this method has the same crystallinity than MOF MIL-101-Cr prepared by the method using hydrofluoric acid.

The state of the art known to the applicant, represented mainly by the technologies described in the patent documents referred, obviously exceeded by the present invention, as in said prior art there is no processes to obtaining MOF materials MIL-101-Cr and MOF MIL-101-Cr-$M^{X+}$ where $M^{X+}$ can be any metal cation, such as $Mg^{2+}$, $Al^{3+}$ or $Ti^{4+}$, employing for its synthesis metal epoxides and alkoxides, avoiding the use of hydrofluoric acid (HF) or bases as synthesis controlling agents.

It is therefore an object of the present invention to provide a process for obtaining materials MOF MIL-101-Cr and MOF MIL-101-Cr-$M^{X+}$ where $M^{X+}$ can be any metal cation, such as $Mg^{2+}$, $Al^{3+}$ or $Ti^{4+}$, employing for its synthesis metal epoxides and alkoxides, avoiding the use of hydrofluoric acid (HF) or bases as synthesis controlling agents.

It is another object of the present invention to provide a process for obtaining MOF materials MIL-101-Cr and MOF MIL-101-Cr-$M^{X+}$ where $M^{X+}$ can be any metal cation, such as $Mg^{2+}$, $Al^{3+}$ or $Ti^{4+}$, 100% pure, with controlled mesoporosity associated with a hysteresis $P/P_0$ from 0.7 to 0.99, BET surface area from 2,500 to 3,500 $m^2/g$, pore volume from 1.1 to 2.2 $cm^3/g$, and pore diameter from 15 to 55 nm.

DETAILED DESCRIPTION

The present invention relates to a process for obtaining materials with Metal Organic atomic structure and called MOF (Metal Organic Framework) type MIL-101-Cr and MIL-101-Cr-$M^{X+}$ (MIL: Material from Institute Lavoisier), where $M^{X+}$ can be any metal cation, such as $Mg^{2+}$, $Al^{3+}$ or $Ti^{4+}$, using for its synthesis metal epoxides and alkoxides, avoiding the use of hydrofluoric acid (HF) or bases as synthesis controlling agents.

By the synthesis process of the present invention are obtained materials such MOF MIL-101-Cr and MOF MIL-101-Cr-$M^{X+}$, 100% pure, with controlled mesoporosity associated with a hysteresis $P/P_0$ from 0.7 to 0.99, BET surface area from 2,500 to 3,500 $m^2/g$, pore volume from 1.1 to 2.2 $cm^3/g$, and pore diameter of 15 to 55 nm.

Among epoxides employed by the present invention is propylene oxide, which is used as a proton scavenger agent and promotes the formation of materials type MOF MIL-101-Cr having high crystallinity and high specific area.

Propylene oxide is used in the synthesis of metal oxides by sol-gel method. In the traditional sol-gel method is used as cation source a metal alkoxide, which is dissolved in alcohol and the hydrolysis is carried out in acidic or basic medium. Acid function is to control the hydrolysis rate, accelerating it by protonation of the oxygen and generate better leaving groups and thus takes place before it happens the condensation reaction of -M-OH-M species. It is well known that this synthesis method generates materials based on metal oxides with exceptional properties and can be considered a "custom design" method. However, the big problem is that the metal alkoxides are very sensitive to moisture, so its management must be very careful for obtaining the expected and reproducible results.

However, in the case of the present invention, the reaction system is much more complex, since in addition to the formation of metal hydroxides clusters, in this case $Cr(OH)_x$, these should be subsequently reacted with an aromatic dicarboxylic acid as an organic binder, preferably terephthalic acid ($H_2BDC$), through the carboxyl groups, under hydrothermal conditions, 180° C. and autogenous pressure of 180 psi.

In the present invention for the synthesis of MOF MIL-101-Cr having high crystallinity and without the use of hydrofluoric acid (HF) or a base such as tetramethylammonium hydroxide (TMAOH), it state that the epoxide plays a crucial role in forming clusters $Cr(OH)_x$ of size and shape suitable to react with the carboxyl groups, COON, of aromatic dicarboxylic acid, preferably terephthalic acid ($H_2BDC$). Epoxide act as proton scavenger during the cluster formation and its reaction with aromatic dicarboxylic acid generates rigid and highly porous structures. The fact that the reaction between the clusters of $Cr(OH)_x$ and the aromatic dicarboxylic acid, preferably terephthalic acid ($H_2BDC$) is carried out under high temperature, 180° C. and hydrothermal conditions to self-generated pressure, is indicative that the reaction between the inorganic cluster $Cr(OH)_x$ and the organic binder, preferably terephthalic acid ($H_2BDC$) is difficult. Therefore, addition of the epoxide provides said reaction to give a material of high crystallinity and high surface area, such as that shown in FIGS. 1 to 8, BET area of at least 2,800 m$^2$/g.

However, the present invention employs metal alkoxides such as $Mg(O-CH_2-CH_3)2$, to incorporate from synthesis metal cations $M^{X+}$, such as $Mg^{2+}$, $Al^{3+}$ or $Ti^{4+}$, within the structure of materials type MOF MIL-101-Cr. This allows incorporate cations, such as Mg, Si, Al, Ti or others, so that remain incorporated in the atomic structure of MOF in orderly manner and highly dispersed, thereby obtaining functionalized materials according to the final application of the material.

In the incorporation of metal cations from the synthesis, metal alkoxides M-OR are used, in which in a very similar way to epoxides, oxygen is protonated and M-OH-M and an alcohol ROH is formed. This causes the cations present in the alkoxide react and incorporate to $CrOH_x$ clusters. The synthesis of MOF-101 MIL-Cr—Mg, generates a material having high crystallinity and high surface area with highly dispersed $Mg^{2+}$. The diffraction pattern of this material no reveals the presence of the phase $Mg(OH)_2$ such as that shown in FIG. 7. This material has a high surface area, such as that shown in FIG. 8, of 2800 m$^2$/g.

The original synthesis of MOF-101 MIL-Cr consist of the hydrothermal reaction of 1,4-benzene dicarboxylate ($H_2BDC$) with chromium nitrate ($Cr/(NO_3)_3.9H_2O$), hydrofluoric acid (HF) and water ($H_2O$) for 8 hours at 220° C. producing a highly crystalline pure chromium terephthalate powder with formula $Cr_3F(H_2O)_2O[(O_2C)-C_6H_4-(CO_2)]_3.nH_2O$ (n=25), based on chemical analysis. The cubic structure of this material (8.9 nm) has several unprecedented features: a mesoporous zeotype architecture, very large cell volume (702 nm3), very large pore sizes (diameters of 2.9-3.4 nm, pore volumes of 12.7-20.6 nm3) and a record adsorption capacity ($S_{Langmuir}$=5,600 to 6,200 m$^2$/g) (O. I. Lebedev, et al. First Direct Imagen of Giant Pores of the Metal-Organic Framework MIL-101. Chem. Mater. 2005, 17, 6525-6527).

Figure 9:
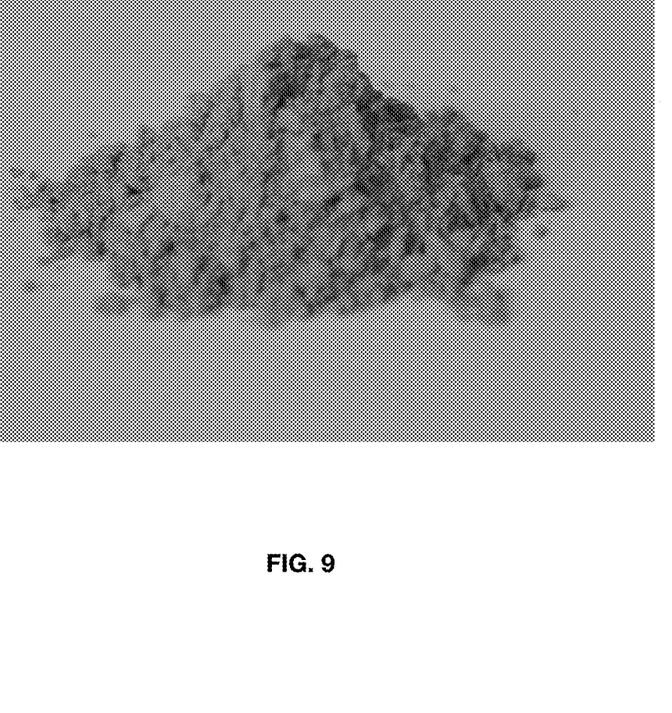
FIG. 9. MOF material MIL-101-Cr synthesized, powder material, as obtained in the synthesis, Example 1.

The materials obtained by the present invention, with atomic Metal Organic structure MIL-101-Cr and MIL-101-Cr-$M^{X+}$, where $M^{X+}$ can be any metal cation, such as $Mg^{2+}$, $Al^{3+}$ or $Ti^{4+}$, are a green fine powder, such as MOF MIL-101-Cr shown in FIG. 9, which was synthesized with propylene oxide.

The process of the present invention for the preparation of materials MOF MIL-101-Cr and MOF MIL-101-Cr-$M^{X+}$ where $M^{X+}$ can be any metal cation, such as Me$^+$, $Al^{3+}$ or $Ti^{4+}$, consisting of:

a) Synthesizing MOF MIL-101-Cr with epoxides, or Synthesizing MOF MIL-101-Cr-$M^{X+}$ with metal alkoxides; and b) Purifying synthesized MOF, in order to obtain 100% pure materials with controlled mesoporosity associated with a hysteresis $P/P_0$ from 0.7 to 0.99, BET surface area from 2,500 to 3,500 m$^2$/g, pore volume from 1.1 to 2.2 cm$^3$/g, and pore diameter from 15-55 nm.

Where:

The synthesis of MOF MIL-101-Cr with epoxides comprising:

adding water to a reactor, preferably demineralized and start constant agitation at room temperature;

adding an aromatic dicarboxylic acid as organic binder, preferably terephthalic acid ($H_2BDC$), and stirring for 5-15 minutes, preferably 8-12 minutes; applying pulses, preferably with an ultrasound probe with 75 to 85% amplitude for a time of 4 to 8 minutes, preferably 5 to 7 minutes, to improve the solubility of aromatic dicarboxylic acid used;

adding a chromium salt, preferably chromium nitrate ($Cr(NO_3)_3.9H_2O$), maintaining stirring for 10 to 30 minutes, preferably for 15 to 25 minutes; applying pulses, preferably with an ultrasound probe with 75 to 85% amplitude for a time of 4 to 8 minutes, preferably 5 to 7 minutes, to the final solution;

adding an epoxide as proton scavenger agent, preferably propylene oxide, to the solution and stirring for 5 to 15 minutes, preferably 8 to 12 minutes;

pouring the final solution in the reactor and closing the reactor to start the hydrothermal treatment for 20 to 28 hours, at 170-190° C., 150 to 250 rpm and autogenous pressure of 160 to 200 psi, preferably for 22 to 26 hours at 175-185° C., 175-225 rpm and autogenous pressure of 170-190 psi; and allowing to cool the reactor to room temperature and recovering the final reaction mixture.

in order to obtain a highly dispersed material having high crystallinity and high surface area, with low residue concentrations of raw materials remained unreacted, so it is important to carry out a purification process of synthesized MOF.

The synthesis of MOF MIL-101-Cr-$M^{X+}$ with metal alkoxides, consisting of:

adding water to the reactor, preferably demineralized and initiate constant agitation at room temperature;

adding a chromium salt, preferably chromium nitrate ($Cr(NO_3)_3.9H_2O$), and an aromatic dicarboxylic acid, preferably terephthalic acid ($H_2BDC$), and stirring for 5 to 15 minutes, preferably 8 to 12 minutes; applying pulses, preferably with an ultrasound probe with 75 to 85% amplitude for a time of 4 to 8 minutes, preferably 5 to 7 minutes, to improve the solubility of the aromatic dicarboxylic acid used;

adding a metal alkoxide, preferably magnesium ethoxide and dissolve maintaining stirring for 5 to 15 minutes, preferably 8 to 12 minutes; applying pulses, preferably with an ultrasound probe with 75 to 85% amplitude for a time of 4 to 8 minutes, preferably 5 to 7 minutes, to the final solution;

pouring the final solution in the reactor and closing the reactor to start the hydrothermal treatment for 20 to 28 hours, at 170-190° C. with no stirring and autogenous pressure preferably for 22 to 26 hours at 175-185° C. without stirring and autogenous pressure; and allowing to cool the reactor and recover the sample.

in order to obtain a highly dispersed material having high crystallinity and high surface area, with metal cation ($M^{X+}$, such as $Mg^{2+}$, $Al^{3+}$ or $Ti^{4+}$), with low residue concentrations of raw materials remained unreacted, so it is important to carry out a purification process of synthesized MOF.

The synthesis processes of the present invention provide a yield of 95 to 98% weight.

Waste of raw materials remained unreacted in synthesized MOF can not be identified by X-ray diffraction, due to its low concentration, so it is important to perform a purification process to achieve 100% purity of material.

Purification of synthesized MOF comprises:
performing a first washing adding 25 to 250 ml of acetone, preferably 175 to 225 ml when the synthesis is performed with epoxides and 35 to 65 ml when synthesis is performed with metal alkoxides, to the resulting synthesis mixture comprising liquid and MOF as suspension; stirring the mixture for 30 to 90 minutes, preferably 50 to 70 minutes, then filtering the mixture;
subjecting the recovered green solid to a second washing with the same characteristics as the first wash, and filtering again;
drying the recovered powder at 100-140° C. for 10 to 14 hours, preferably at 110-130° C. for 11 to 13 hours.

in order to obtain a pure 100% free waste material having high crystallinity and high surface area, with highly dispersed metal cation ($M^{X+}$, such as $Mg^{2+}$, $Al^{3+}$ or $Ti^{4+}$).

By the synthesis process of the present invention, materials type MOF MIL-101-Cr and MOF MIL-101-Cr-$M^{X+}$ 100% pure, with controlled mesoporosity associated with a hysteresis $P/P_0$ from 0.7 to 0.99, BET surface area from 2,500 to 3,500 $m^2/g$, pore volume from 1.1 to 2.2 $cm^3/g$, and pore diameter form 15 to 55 nm.

In this regard it should be noted that the mesoporosity is a very important property in catalytic and adsorbent materials, so it is very important to control.

In the present invention, the mesoporosity is a function of the synthesis controlling agents: metal epoxides and alkoxides, critical property to custom design materials.

EXAMPLES

The following some practical examples for a better understanding of the present invention are described, without limiting its scope.

Example 1

MOF Synthesis of MIL-101-Cr with Propylene Oxide.

In a 1-liter beaker, 660 ml of demineralized water were added, constant magnetic stirring at room temperature was initiated. 22.174 g of terephthalic acid ($H_2BDC$) were added and stirred for 10 minutes. Pulses with the ultrasound probe SONICS Vibra Cell with 80% amplitude was applied for an effective time of 6 minutes to improve the solubility of terephthalic acid. 52.879 g of chromium nitrate ($Cr(NO_3)_3 \cdot 9H_2O$) was weighed, and added to the above solution while stirring for 20 minutes. Pulses with SONICS Vibra Cell ultrasound probe with 80% amplitude were applied for an effective time of 6 minutes at a final solution. 1.938 g of propylene oxide were added and the solution was stirred for 10 min. The final solution was poured into the 1-liter beaker of Parr reactor, which contains in its interior a Teflon beaker. The Parr reactor was closed to start the hydrothermal treatment for 24 hours at 180° C., 200 rpm and autogenous pressure. After the reaction, the reactor was allowed to cool to room temperature and the final reaction mixture was recovered.

Purification of Synthesized MOF: Wash with Acetone.

To the resulting synthesis mixture comprising liquid and MOF as suspension were added 200 ml of acetone. The mixture was stirred for one hour and then filtered and the recovered green solid was placed in a flask and were added 200 ml of acetone to a second washing and filtered again. The recovered powder was dried at 120° C. for 12 hours.

Figure 1:
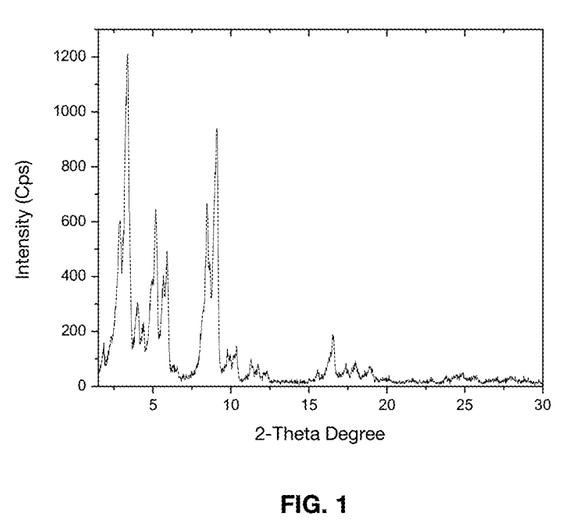
FIG. 1. X-ray diffraction pattern of MOF material MIL-101-Cr synthesized with propylene oxide, Example 1.
Figure 2:
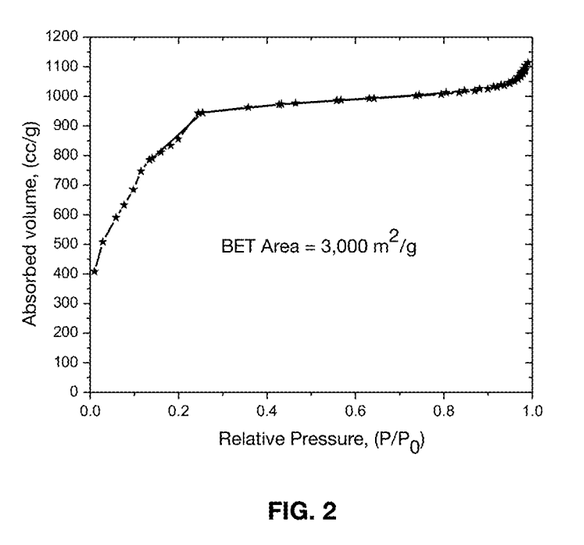
FIG. 2. N2 adsorption isotherm corresponding to MOF material MIL-101-Cr, synthesized with propylene oxide, Example 1.

FIGS. 1 and 2 show the X-ray diffraction pattern and the N2 adsorption isotherm respectively of MOF material MIL-101-Cr synthesized with propylene oxide, which show the following properties, according to BET method: surface area of 3,000 $m^2/g$, pore volume of 1.269 $cm^3/g$, and pore diameter of ≈50 nm.

FIG. 9 shows the powder material obtained: MIL MOF-101 (Cr) synthesized with propylene oxide.

Example 2

Synthesis of MOF MIL-101-Cr with Propylene Oxide.

Following the same procedure of Example 1, the content of propylene oxide was increased to 3.08 g, keeping the amounts of water in 600 ml, $H_2BDC$ in 22.174 g $Cr(NO_3)_3 \cdot 9H_2O$ at 52.879 g.

The reactant solution was poured into the 1-liter beaker of Parr reactor, which contains in its interior a Teflon beaker. The Parr reactor was closed to start the hydrothermal treatment for 24 hours at 180° C., 200 rpm and autogenous pressure. After the reaction, the reactor was allowed to cool to room temperature and the final reaction mixture was recovered.

Purification of Synthesized MOF: Wash with Acetone.

To the resulting synthesis mixture comprising liquid and MOF as suspension were added 200 ml of acetone. The mixture was stirred for one hour and then filtered and the recovered green solid was placed in a flask and were added 200 ml of acetone to a second washing and filtered again. The recovered powder was dried at 120° C. for 12 hours.

Figure 3:
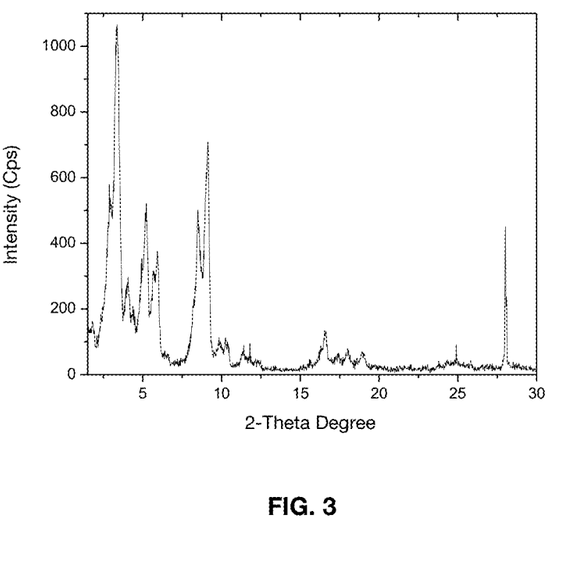
FIG. 3. X-ray diffraction pattern of MOF material MIL-101-Cr synthesized with propylene oxide, Example 2.
Figure 4:
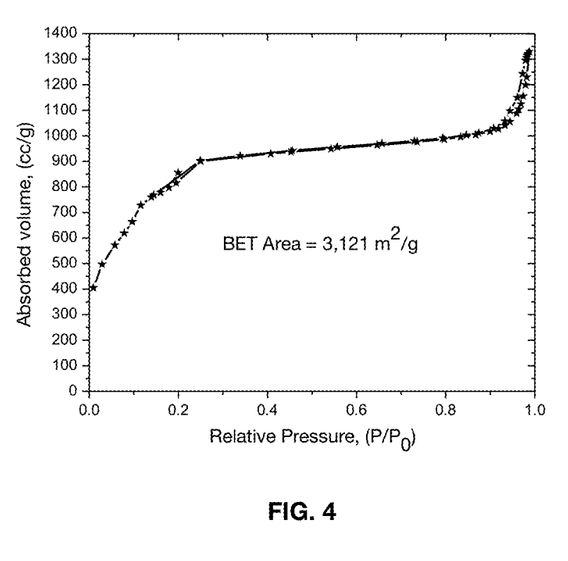
FIG. 4. N2 adsorption isotherm corresponding to MOF material MIL-101-Cr synthesized with propylene oxide, Example 2.

FIGS. 3 and 4 show the X-ray diffraction pattern and the N2 adsorption isotherm respectively of MOF material MIL-101-Cr synthesized with propylene oxide, which present the following characteristics, according to the BET method: surface area of 3,121 $m^2/g$, pore volume of 1.833 $cm^3/g$, 10% more than in the case of Example 1, and pore diameter of ≈50 nm which is in the range of mesopores. It is to be noted that the adsorption isotherm, FIG. 4, reveals the presence of mesoporosity associated with a hysteresis $P/P_0$ from 0.9 to 0.98.

The powder obtained is similar to that shown in FIG. 9.

Example 3

Synthesis of MOF MIL-101-Cr with Propylene Oxide.

Following the same procedure of Example 1, the content of propylene oxide was increased to 4.11 g, keeping the amounts of water in 600 ml, $H_2BDC$ in 22.174 g, $Cr(NO_3)_3 \cdot 9H_2O$ in 52.879 g.

The reactant solution was poured into the 1-liter beaker of Parr reactor, which contains in its interior a Teflon baker. The Parr reactor was closed to start the hydrothermal treatment for 24 hours at 180° C., 200 rpm and autogenous pressure. After the reaction, the reactor was allowed to cool to room temperature and the final reaction mixture was recovered.

Purification of Synthesized MOF: Wash with Acetone.

To the resulting synthesis mixture comprising liquid and MOF as suspension were added 200 ml of acetone. The mixture was stirred for 1 hour and then filtered and the recovered green solid was placed in a flask and were added 200 ml of acetone to a second washing and filtered again. The recovered powder was dried at 120° C. for 12 hours.

Figure 5:
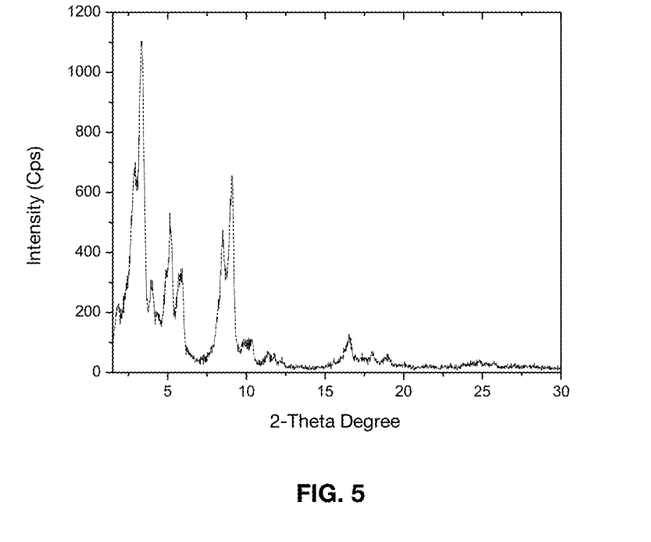
FIG. 5. X-ray diffraction pattern of MOF material MIL-101-Cr synthesized with propylene oxide, Example 3.
Figure 6:
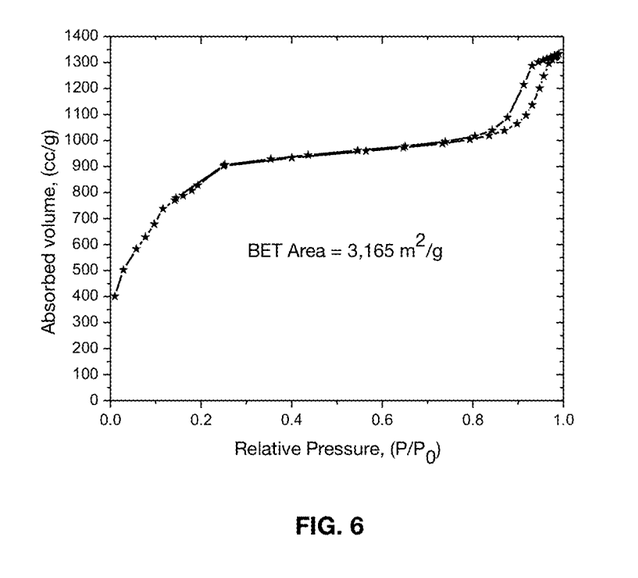
FIG. 6. N2 adsorption isotherm corresponding to MOF material MIL-101-Cr synthesized with propylene oxide, Example 3.

FIGS. 5 and 6 show the X-ray diffraction pattern and N2 adsorption isotherm respectively, of MOF material MIL-101-Cr synthesized with propylene oxide, which presented the following characteristics, according to the BET method: surface area of 3,165 m$^2$/g, pore volume of 2.045 cm$^3$/g, 20% more porous than in the case of Example 1, and pore diameter of ≈20 nm. It is important to note that the adsorption isotherm, FIG. 6, reveals the presence of mesoporosity, associated with a much stronger hysteresis than that obtained in Example 2, P/P$_0$ from 0.8 to 0.98 indicating that the mesoporosity is much more important in this material.

The foregoing confirms that the property of mesoporosity is based on the content of propylene oxide, so it can be modulated according to the needs of the material application; that is, this feature is very important to custom design materials.

The powder obtained is similar to that shown in FIG. 9.

Example 4

Synthesis of MOF MIL-101-Cr—Mg with Magnesium Ethoxide (Mg(OCH$_2$CH$_3$)$_2$).

In a 100 ml beaker, 50 ml of demineralized water were added, constant magnetic stirring at room temperature was initiated. 3.97 g of chromium nitrate (Cr(NO$_3$)$_3$.9H$_2$O) was weighed and added. 1.65 g of terephthalic acid (H$_2$BDC) were weighed and added to the above solution under constant stirring for 10 minutes. Pulses with the SONICS Vibra Cell ultrasound probe with 80% amplitude was applied for an effective time of 6 minutes to improve the solubility of terephthalic acid. Finally, 0.36 g of magnesium ethoxide (Mg(OCH$_2$CH$_3$)$_2$) was added, and dissolved with stirring for 10 minutes. Pulses with Sonics Vibra Cell ultrasound probe with 80% amplitude were applied for an effective time of 6 minutes to final solution. The final solution was poured into the 100 milliliter beaker of Parr reactor, which contains in its interior a Teflon beaker. The Parr reactor was closed to start the hydrothermal treatment for 24 hours at 180° C. without stirring and autogenous pressure. After the reaction, the reactor was cooled and the sample was recovered.

Purification of Synthesized MOF: Wash with Acetone.

To the resulting synthesis mixture comprising liquid and MOF as suspension were added 50 ml of acetone. The mixture was stirred for one hour and then filtered and the recovered green solid was placed in a flask and were added 50 ml of acetone to a second washing and filtered again. The recovered powder was dried at 120° C. for 12 hours.

Figure 7:
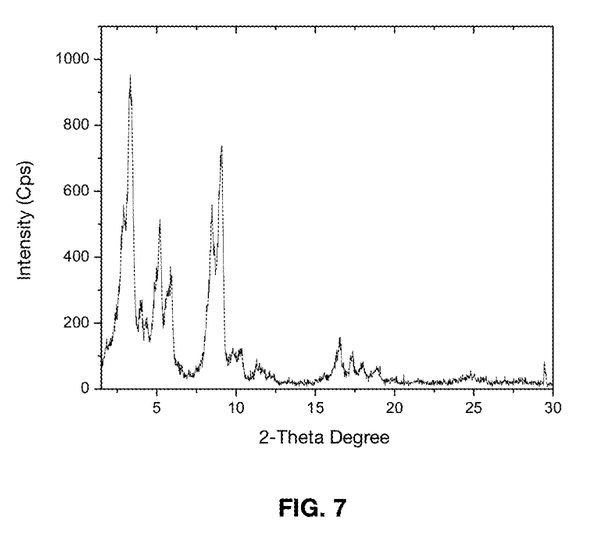
FIG. 7. X-ray diffraction pattern of MOF material MIL-101-Cr—Mg synthesized and functionalized with magnesium ethoxide, Example 4.
Figure 8:
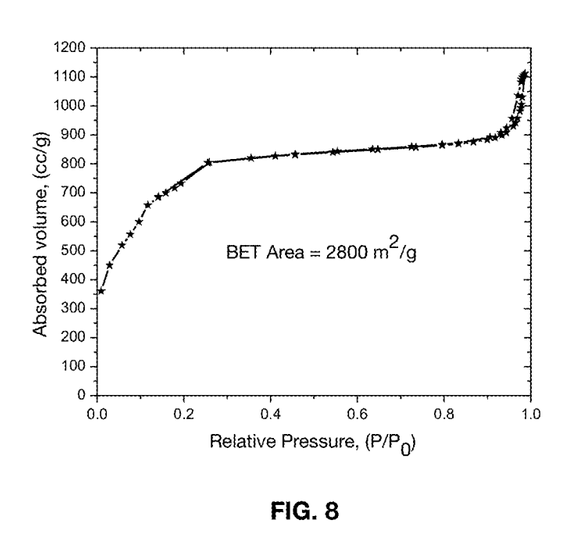
FIG. 8. N2 adsorption isotherm corresponding to MOF material MIL-101-Cr—Mg synthesized and functionalized with magnesium ethoxide, Example 4.

FIGS. 7 and 8 show the X-ray diffraction pattern and the N2 adsorption isotherm respectively of MOF material MIL-101-Cr—Mg synthesized and functionalized with magnesium ethoxide (Mg(OCH$_2$CH$_3$)$_2$) which present the following characteristics, according to the BET method: surface area of 2,800 m$^2$/g, pore volume of 1.269 cm$^3$/g, and pore diameter of ≈50 nm. It is important to note that the adsorption isotherm, FIG. 8, shows the presence of mesoporosity, associated with a hysteresis P/P$_0$ from 0.9 to 0.98 indicating that the mesoporous material has features comparable to those of the material obtained in Example 2.

The powder obtained is similar to that shown in FIG. 9.

The invention claimed is:

1. A process for obtaining a metal-organic framework of chromium(III) terephthalate (MIL-101-Cr) or a metal-organic framework of chromium(III) terephthalate with an additional metal ion M$^{X+}$ (MIL-101-Cr-M$^{X+}$), consisting of:
   a) Synthesizing the MIL-101-Cr with epoxides, or Synthesizing the MIL-101-Cr M$^{X+}$ with metal alkoxides, where M$^{X+}$ is any metal cation; and
   b) Purifying the synthesized MIL-101-Cr or MIL-101-Cr-M$^{X+}$;
   in order to obtain 100% pure materials with controlled mesoporosity associated with a hysteresis P/P$_0$ from 0.7 to 0.99, BET surface area from 2,500 to 3,500 m$^2$/g, pore volume from 1.1 to 2.2 cm$^3$/g, and pore diameter from 15 to 55 nm.

2. The process of claim 1, wherein step a) for synthesizing MIL-101-Cr comprises:
   adding water to a mixing tank, and starting constant stirring at room temperature;
   adding terephthalic acid, and stirring 5-15 minutes;
   adding a chromium salt, maintaining stirring for 10 to 30 minutes, and applying pulses with an ultrasound probe with 75 to 85% amplitude for a time of 4 to 8 minutes, to form a solution;
   adding an epoxide, to the solution and stirring for 5 to 15 minutes to form a final solution;
   pouring the final solution in to a reactor and closing the reactor to start hydrothermal treatment for 20 to 28 hours, at 170-190° C., 150 to 250 rpm and at autogenous pressure of 160 to 200 psi; and
   allowing the reactor to cool to room temperature and recovering a final reaction mixture.

3. The process of claim 1, wherein step a) for synthesizing MIL-101-Cr-M$^{X+}$ consists of:
   adding water to a mixing tank and initiating constant stirring at room temperature;
   adding a chromium salt and terephthalic acid, and stirring for 5 to 15 minutes and applying pulses with an ultrasound probe with 75 to 85% amplitude for a time of 4 to 8 minutes;
   adding a metal alkoxide and dissolving while maintaining stirring for 5 to 15 minutes, applying pulses with an ultrasound probe with 75 to 85% amplitude for a time of 4 to 8 minutes to form a final solution;
   pouring the final solution in a reactor and closing the reactor to start hydrothermal treatment for 20 to 28 hours, at 170-190° C. with no stirring and at autogenous pressure; and
   allowing the reactor to cool and recovering a sample.

4. The process of claim 1, wherein step a) provides a yield of 95 to 98% weight.

5. The process of claim 1, wherein step b) comprises:
   performing a first washing by adding 25 to 250 ml of acetone to the synthesized MIL-101-Cr or MIL-101-Cr-M$^{X+}$ to provide a mixture comprising liquid and MIL-101-Cr or MIL-101-Cr-M$^{X+}$ as suspension; stirring the mixture for 30 to 90 minutes, then filtering the mixture to recover a solid;
   subjecting the recovered solid to a second washing with the same characteristics as the first wash, and filtering again to recover a powder; and
   drying the recovered powder at 100-140° C. for 10 to 14 hours.

6. The process of claim 1, wherein M$^{X+}$ is selected from Mg$^{2+}$, Al$^{3+}$ and Ti$^{4+}$.

7. The process of claim 2, wherein the stirring step further comprises applying pulses with an ultrasound probe with 75 to 85% amplitude for a time of 4 to 8 minutes.

8. The process of claim 2, wherein the chromium salt is $Cr(NO_3)_3 \cdot 9H_2O$.

9. The process of claim 2, wherein the epoxide is propylene oxide.

10. The process of claim 2, wherein the hydrothermal treatment in the reactor is conducted for 22 to 26 hours at 175-185° C., 175-225 rpm and autogenous pressure of 170-190 psi.

11. The process of claim 3, wherein the chromium salt is $Cr(NO_3)_3 \cdot 9H_2O$.

12. The process of claim 3, wherein the metal alkoxide is $Mg(OCH_2CH_3)_2$.

13. The process of claim 3, wherein the hydrothermal treatment in the reactor is conducted for 22 to 26 hours at 175-185° C. without stirring and at autogenous pressure.

14. The process of claim 2, wherein step b) comprises:
performing a first washing by adding 175 to 225 ml of acetone to the synthesized MIL-101-Cr$^+$ to provide a mixture comprising liquid and MIL-101-Cr as suspension; stirring the mixture for 30 to 90 minutes, then filtering the mixture to recover a solid;
subjecting the recovered solid to a second washing with the same characteristics as the first wash, and filtering again to recover a powder; and
drying the recovered powder at 100-140° C. for 10 to 14 hours.

15. The process of claim 3, wherein step b) comprises:
performing a first washing by adding 35 to 65 ml of acetone to the synthesized MIL-101-Cr-M$^{x+}$ to provide a mixture comprising liquid and MIL-101-Cr-M$^{x+}$ as suspension; stirring the mixture for 30 to 90 minutes, then filtering the mixture to recover a solid;
subjecting the recovered solid to a second washing with the same characteristics as the first wash, and filtering again to recover a powder; and
drying the recovered powder at 100-140° C. for 10 to 14 hours.

* * * * *